US012668558B2

(12) United States Patent
Luo et al.

(10) Patent No.: US 12,668,558 B2
(45) Date of Patent: Jun. 30, 2026

(54) REACTOR SYSTEM FOR ACETYLENE ABSORPTION AND SELECTIVE HYDROGENATION

(71) Applicant: Chevron U.S.A. Inc., San Ramon, CA (US)

(72) Inventors: Huping Luo, Moraga, CA (US); Xiaoying Ouyang, Albany, CA (US); Christopher Declan Lane, El Cerrito, CA (US); Howard Steven Lacheen, Richmond, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 19/214,523

(22) Filed: May 21, 2025

(65) Prior Publication Data

US 2026/0028297 A1     Jan. 29, 2026

Related U.S. Application Data

(60) Provisional application No. 63/674,420, filed on Jul. 23, 2024.

(51) Int. Cl.
| | |
|---|---|
| *C07C 5/09* | (2006.01) |
| *C07C 7/10* | (2006.01) |
| *C07C 7/11* | (2006.01) |

(52) U.S. Cl.
CPC .................. *C07C 5/09* (2013.01); *C07C 7/10* (2013.01); *C07C 7/11* (2013.01)

(58) Field of Classification Search
CPC ................ C07C 5/09; C07C 7/10; C07C 7/11

(Continued)

(56) References Cited

U.S. PATENT DOCUMENTS 8,013,197 B2 *   9/2011   Peterson ................. C07C 7/163
585/277

FOREIGN PATENT DOCUMENTS

| | | | | |
|---|---|---|---|---|
| CN | 105418352 A | * | 3/2016 | ............... C07C 5/09 |
| CN | 105967969 A | | 9/2016 | |

(Continued)

OTHER PUBLICATIONS

PCT/US2025/030342, International Search Report, Sep. 23, 2025, 14 pages.

*Primary Examiner* — Prem C Singh
*Assistant Examiner* — Francis C Campbell
(74) *Attorney, Agent, or Firm* — Michael E. Carmen; Terrence M. Flaherty

(57)     ABSTRACT

A system including an acetylene absorption and hydrogenation reactor configured to receive an acetylene-rich gas stream and a hydrogen stream flowing upwards or downwards to a reaction zone and a cooled liquid solvent flowing downwards to the reaction zone, wherein the cooled recycled liquid solvent stream extracts acetylene in the acetylene-rich gas stream and hydrogen in the hydrogen stream and at least a portion of the acetylene is converted to ethylene in the presence of a hydrogenation catalyst and hydrogen under hydrogenation reaction conditions to produce an acetylene-lean gas effluent and a heated liquid solvent effluent, and a first heat exchanger for receiving the heated liquid solvent effluent, the first heat exchanger being configured to remove heat from the heated liquid solvent effluent and produce the cooled recycled liquid solvent stream as part of a continuous solvent recycle loop.

9 Claims, 2 Drawing Sheets

(58) Field of Classification Search
USPC ........................................................ 585/259
See application file for complete search history.

(56)                     References Cited

FOREIGN PATENT DOCUMENTS

| CN | 106748616 A | 5/2017 |
| CN | 106986738 A | 7/2017 |

* cited by examiner

REACTOR SYSTEM FOR ACETYLENE ABSORPTION AND SELECTIVE HYDROGENATION

PRIORITY CLAIM

The present application claims priority to U.S. Provisional Patent Application Ser. No. 63/674,420, entitled "Reactor System for Acetylene Absorption and Selective Hydrogenation," filed Jul. 23, 2024, the content of which is incorporated by reference herein in its entirety.

BACKGROUND

The ongoing search for alternatives to crude is increasingly driven by a number of factors. These include diminishing petroleum reserves, higher anticipated energy demands, and heightened concerns over greenhouse gas emissions from sources of non-renewable carbon. In view of its abundance in natural gas reserves, as well as in gas streams obtained from biological sources (biogas), natural gas has become the focus of a number of possible routes for providing liquid hydrocarbons. Natural gas occurs underground and is present as a gas when it comes out of the ground. Natural gas primarily consists of methane ($CH_4$), and additionally some other hydrocarbons such as ethane ($C_2H_6$) and propane ($C_3H_8$). Accordingly, converting light hydrocarbons such as methane to high value products such as hydrogen, olefins and aromatics has become an attractive option.

SUMMARY

In accordance with an illustrative embodiment, a system comprises:

an acetylene absorption and hydrogenation reactor configured to receive an acetylene-rich gas stream and a hydrogen stream flowing upwards or downwards to a reaction zone and a cooled recycled liquid solvent stream flowing downwards to the reaction zone, wherein the cooled recycled liquid solvent stream extracts acetylene in the acetylene-rich gas stream and hydrogen in the hydrogen stream and at least a portion of the acetylene is converted to ethylene in the presence of a hydrogenation catalyst and the hydrogen under hydrogenation reaction conditions to produce an acetylene-lean gas effluent and a heated liquid solvent effluent, and a first heat exchanger in fluid communication with the acetylene absorption and hydrogenation reactor for receiving the heated liquid solvent effluent, the first heat exchanger being configured to remove heat from the heated liquid solvent effluent and produce the cooled recycled liquid solvent stream as part of a continuous solvent recycle loop.

In accordance with another illustrative embodiment, a system comprises:

an acetylene absorption and hydrogenation reactor configured to receive an acetylene-rich gas stream and a hydrogen stream flowing upwards or downwards to a reaction zone and a cooled recycle liquid solvent stream flowing downwards to the reaction zone, wherein the cooled recycled liquid solvent stream extracts acetylene in the acetylene-rich gas stream and hydrogen in the hydrogen stream and at least a portion of the extracted acetylene is converted to ethylene in the presence of a hydrogenation catalyst and the hydrogen under hydrogenation reaction conditions to produce an acetylene-lean gas effluent and a heated liquid solvent effluent comprising a liquid solvent and one or more impurities, a first heat exchanger in fluid communication with the acetylene absorption and hydrogenation reactor for receiving at least a first stream of the heated liquid solvent effluent, the first heat exchanger being configured to remove heat from the first stream of the heated liquid solvent effluent and produce the cooled recycled liquid solvent stream, and a separation unit, in fluid communication with the first heat exchanger, configured to receive a second stream of the heated liquid solvent effluent and separate the one or more impurities from the liquid solvent and produce a clean liquid solvent stream.

In accordance with yet another illustrative embodiment, a continuous process comprises:

passing an acetylene-rich gas stream and a hydrogen stream to an acetylene absorption and hydrogenation reactor flowing upwards or downwards to a reaction zone in the acetylene absorption and hydrogenation reactor, passing a cooled recycled liquid solvent stream to the absorption and hydrogenation reactor flowing downwards to the reaction zone in the acetylene absorption and hydrogenation reactor, processing the acetylene-rich gas stream and the hydrogen stream with the cooled recycled liquid solvent stream to extract acetylene in the acetylene-rich gas stream and hydrogen in the hydrogen stream and convert at least a portion of the acetylene to ethylene in the presence of a hydrogenation catalyst and the hydrogen under hydrogenation reaction conditions to produce an acetylene-lean gas effluent and a heated liquid solvent effluent, and passing the heated liquid solvent effluent to a first heat exchanger to remove heat from the heated liquid solvent effluent to produce the cooled recycled liquid solvent stream as part of a continuous solvent recycle loop.

BRIEF DESCRIPTION OF THE DRAWINGS

In combination with the accompanying drawings and with reference to the following detailed description, the features, advantages, and other aspects of the implementations of the present disclosure will become more apparent, and several implementations of the present disclosure are illustrated herein by way of example but not limitation. The principles illustrated in the example embodiments of the drawings can be applied to alternate processes and apparatus. Additionally, the elements and features shown in the drawings are not necessarily to scale, emphasis instead being placed upon clearly illustrating the principles of the example embodiments. Certain dimensions or positions may be exaggerated to help visually convey such principles. In the drawings, the same reference numerals used in different embodiments designate like or corresponding, but not necessarily identical, elements. In the accompanying drawings.

DETAILED DESCRIPTION

Figure 1A:
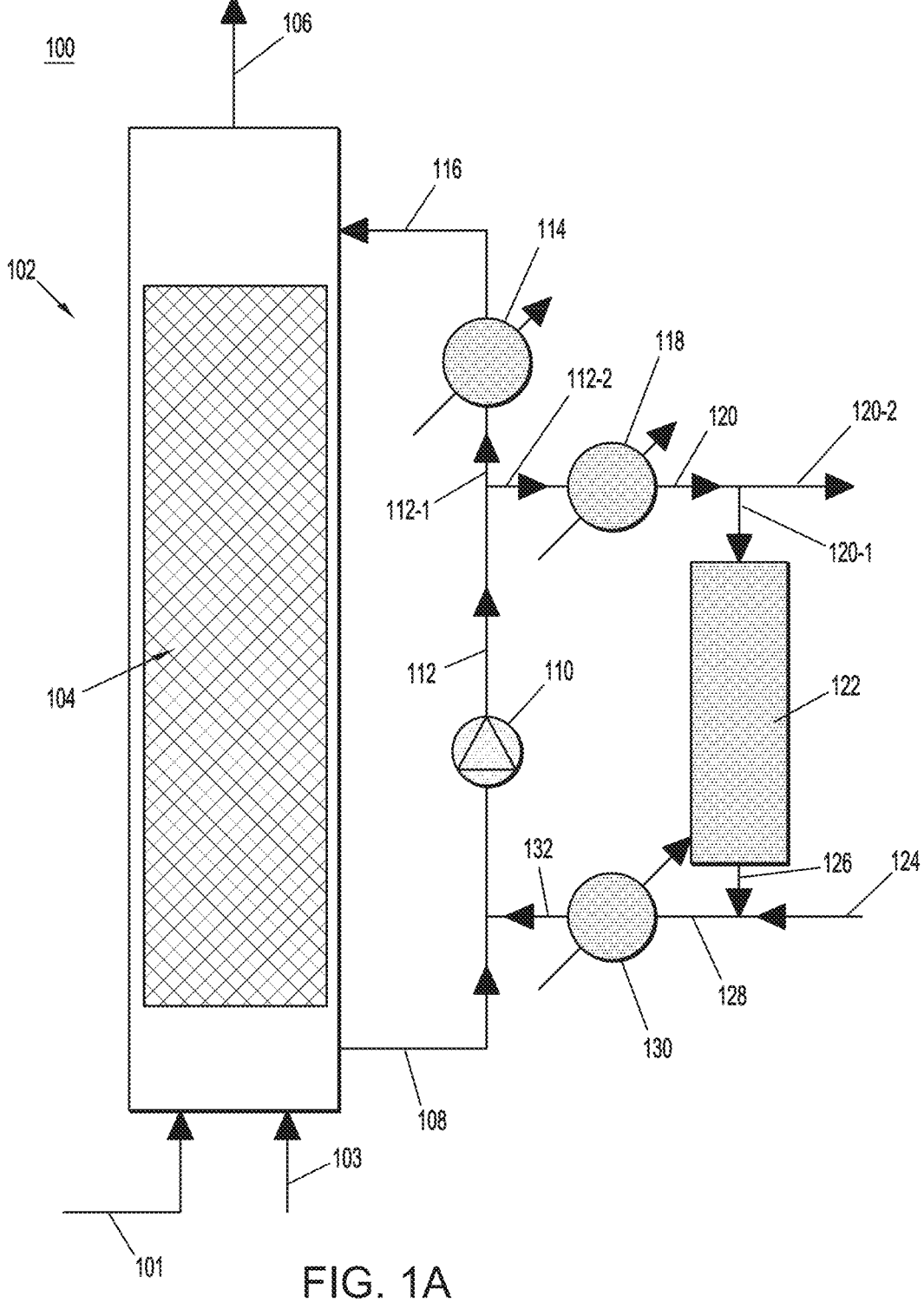
FIG. 1A illustrates a schematic diagram of a system and process for the selective absorption and hydrogenation of acetylene in an acetylene-rich gas stream to ethylene in an acetylene absorption and hydrogenation reactor operating with a continuous solvent recycle loop, according to an illustrative embodiment.

Various illustrative embodiments described herein are directed to acetylene absorption and hydrogenation reactor systems and processes for converting an acetylene-rich gas stream into a hydrogenation effluent comprising ethylene.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology can be applied, as long as that definition does not conflict with any other disclosure or definition applied herein or render indefinite or non-enabled any claim to which that definition is applied. To the extent that any definition or usage provided by any document incorporated herein by reference conflicts with the definition or usage provided herein, the definition or usage provided herein controls.

While systems and processes are described in terms of "comprising" various components or steps, the systems and processes can also "consist essentially of" or "consist of" the various components or steps, unless stated otherwise.

The terms "a," "an," and "the" are intended to include plural alternatives, e.g., at least one. The terms "including," "with," and "having," as used herein, are defined as comprising (i.e., open language), unless specified otherwise.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, all numerical end points of ranges disclosed herein are approximate, unless excluded by proviso.

Values or ranges may be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means ±20% of the stated value, ±15% of the stated value, ±10% of the stated value, ±5% of the stated value, ±3% of the stated value, or ±1% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any members of a claimed group.

The term "continuous" as used herein shall be understood to mean a system that operates without interruption or cessation for a period of time, such as where reactant(s) and catalyst(s) are continually fed into a reaction zone and products are continually or regularly withdrawn without stopping the reaction in the reaction zone.

A "fresh catalyst" as used herein denotes a catalyst which has not previously been used in a catalytic process.

A "spent catalyst" as used herein denotes a catalyst that has less activity at the same reaction conditions (e.g., temperature, pressure, inlet flows) than the catalyst had when it was originally exposed to the process. This can be due to a number of reasons, several non-limiting examples of causes of catalyst deactivation are coking or carbonaceous material sorption or accumulation, steam or hydrothermal deactivation, metals (and ash) sorption or accumulation, attrition, morphological changes including changes in pore sizes, cation or anion substitution, and/or chemical or compositional changes.

A "regenerated catalyst" as used herein denotes a catalyst that had become spent, as defined above, and was then subjected to a process that increased its activity to a level greater than it had as a spent catalyst. This may involve, for example, reversing transformations or removing contaminants outlined above as possible causes of reduced activity. The regenerated catalyst typically has an activity that is equal to or less than the fresh catalyst activity.

The term "zone" can refer to an area including one or more equipment items and/or one or more sub-zones. Equipment items can include one or more reactors or reactor vessels, absorption units, separation vessels, distillation towers, heaters, heat exchangers, pipes, pumps, compressors, and controllers. Additionally, an equipment item, such as a reactor, dryer, or vessel, can further include one or more zones or sub-zones.

The term "effluent" refers to a stream that is passed out of a reactor, a reaction zone, or a separation unit following a particular reaction or separation. Generally, an effluent has a different composition than the stream that entered the reactor, reaction zone, or absorption unit. It should be understood that when an effluent is passed to another component or system, only a portion of that effluent may be passed. For example, a slipstream may carry some of the effluent away, meaning that only a portion of the effluent may enter the downstream component or system.

The term "primarily" shall be understood to mean an amount greater than 50%, e.g., 50.01 to 100%, or any range between, e.g., 51 to 95%, 75% to 90%, at least 60%, at least 70%, at least 80%, etc.

For any figure shown and described herein, one or more of the components may be omitted, added, repeated, and/or substituted. Additionally, it should be understood that in certain cases components of the example systems can be combined or can be separated into subcomponents. Accordingly, embodiments shown in a particular figure should not be considered limited to the specific arrangements of components shown in such figure. Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure.

Direct conversion of light hydrocarbons such as methane ($CH_4$), ethane and propane under non-oxidative conditions can produce higher molecular weight hydrocarbons, such as olefins, alkynes and aromatics (e.g., benzene), as value-added chemicals and at the same time produce hydrogen that can be used to make, for example, clean and zero carbon fuel. Hydrogen is one of the more important options for future clean energy. However, the desired product selectivity obtained from the direct conversion processes will depend on the particular type of catalyst as well as reaction condition. In general, this reaction is highly endothermic with an enthalpy of about 90 KJ/mol of $CH_4$ or 60 KJ/mol of $H_2$, and the exact value of the reaction heat will depend on the desired product distribution. It is also an equilibrium limited reaction, and high temperatures are usually required to achieve a $CH_4$ conversion that would be practical for commercial applications. For example, to be commercially practical, maintaining a reactor at a temperature range of 600° C. to 1200° C. is required to achieve an acceptable methane conversion.

The required heat creates other practical challenges. For example, under such temperature conditions, the production of coke or solid carbon in the reactor becomes common, which can significantly reduce the yield of high value products, as well as cause significant operational issues such as plugging of the reactor and catalyst deactivation. Such high temperatures also can require expensive materials for the reactor and can make design of the reactor challenging.

As a further example, under such high temperature conditions, a substantial amount of acetylene will also be produced during the conversion process along with minor amounts of higher triple bond species and dienes such as $C_3H_4$. Acetylene and ethylene are hydrocarbons with the formula $C_2H_2$ and $C_2H_4$, respectively. They are widely used in the chemical industry, and their worldwide production exceeds that of any other organic compound. In the United States and Europe alone, approximately 90% of ethylene is used to produce ethylene oxide, ethylene dichloride, ethyl benzene and polyethylene. On the other hand, while acetylene could be a high value final product, it is highly unstable. Therefore, separating and purifying acetylene to meet acetylene product specifications could significantly complicate the overall process. As a result, producing ethylene is more desirable than producing acetylene.

In view of these challenges, there is a need for solutions to handle acetylene produced during the conversion process to reduce the associated safety risk as well as simplify the overall process. In addition, it would be advantageous for the reactor design for this process to have the capability to (1) provide the reaction heat needed to maintain an optimized temperature profile to achieve high conversion and (2) regenerate and recycle the catalyst being used. It would further be advantageous if such solutions are more energy efficient than existing approaches to produce hydrogen and value-added chemicals.

Illustrative embodiments address the above and other issues by providing acetylene absorption and hydrogenation reactor systems and processes for converting an acetylene-rich gas stream into a hydrogenation effluent comprising ethylene with a continuous solvent recycle loop. The systems and processes provide many advantages, examples of which are mentioned herein. For example, the non-limiting illustrative embodiments described herein overcome the drawbacks discussed above by providing acetylene absorption and hydrogenation reactor systems and processes for converting a high concentration acetylene-rich gas stream into a hydrogenation effluent comprising ethylene at high conversion and high selectivity. Specifically, the non-limiting illustrative embodiments described herein are directed to systems and processes to selectively extract acetylene from a mixed gas feedstock containing at least a high concentration of acetylene, ethylene, hydrogen, and other light hydrocarbon gases, followed by converting the extracted acetylene into ethylene, to achieve high acetylene conversion and high ethylene selectivity with a continuous solvent recycle loop.

Figure 1B:
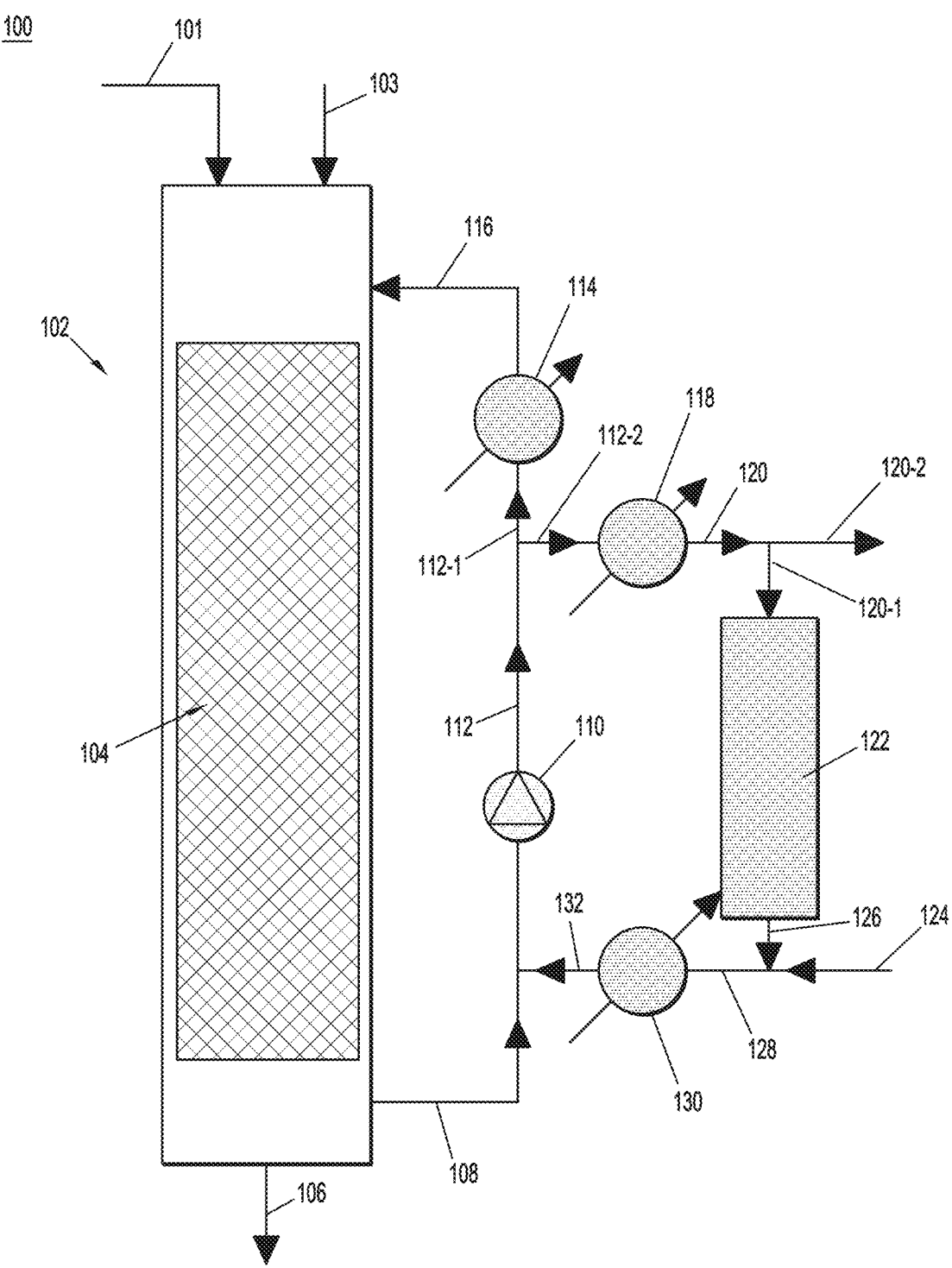
FIG. 1B illustrates a schematic diagram of a system and process for the selective absorption and hydrogenation of acetylene in an acetylene-rich gas stream to ethylene in an acetylene absorption and hydrogenation reactor operating with a continuous solvent recycle loop, according to an illustrative embodiment.

The non-limiting illustrative embodiments of the present disclosure will be specifically described below with reference to the accompanying drawings. For the purpose of clarity, some steps leading up to the production of the hydrogenation effluent comprising ethylene as illustrated in FIGS. 1A and 1B may be omitted. In other words, one or more well-known processing steps which are not illustrated but are well-known to those of ordinary skill in the art have not been included in the figures. This is not intended to be interpreted as a limitation of any particular embodiment, or illustration, or scope of the claims.

Referring now to the drawings in more detail, FIGS. 1A and 1B illustrate details of systems and processes for improved production of a hydrogenation effluent comprising ethylene from acetylene utilizing a system including at least one or more acetylene absorption and hydrogenation reactors, one or more heat exchangers, and one or more pumps. It is to be understood that the system including at least the one or more acetylene absorption and hydrogenation reactors, the one or more heat exchangers, and the one or more pumps is not limited to the configuration of the embodiments shown in FIGS. 1A and 1B, and other configurations are contemplated herein.

Referring now to FIG. 1A, a system 100 includes an acetylene absorption and hydrogenation reactor 102 (hereinafter referred to as "reactor 102") for receiving an acetylene-rich gas stream 101 and a hydrogen stream 103 in a bottom end of reactor 102 and a cooled recycled liquid solvent stream 116 as discussed below in a top end of reactor 102 as part of a continuous solvent recycle loop. However, these entry points are merely illustrative and any point of entry of acetylene-rich gas stream 101, hydrogen stream 103 and cooled recycled liquid solvent stream 116 into reactor 102 is contemplated.

In some embodiments, acetylene-rich gas stream 101 is obtained from the pyrolysis of a light hydrocarbon feed stream comprising methane such as, for example, natural gas. However, this is merely illustrative and any industrial process for producing an acetylene-rich gas stream is contemplated herein. In some embodiments, acetylene-rich gas stream 101 can contain at least a high concentration of acetylene as well as ethylene, methane, hydrogen and other light hydrocarbons. In some embodiments, acetylene-rich gas stream 101 can contain from about 0.1 wt. % to about 5 wt. % of acetylene.

Hydrogen stream 103 includes hydrogen, which is contained in a hydrogen "treat gas," for injecting into reactor 102 to allow sufficient hydrogen vapor pressure in reactor 102 for at least the hydrogenation reaction as discussed below. The treat gas can be either pure hydrogen or a hydrogen-containing gas, which is a gas stream containing hydrogen in an amount that is sufficient for the intended reaction(s), optionally including one or more other gases (e.g., nitrogen and light hydrocarbons such as methane). The treat gas stream introduced into a reaction stage can contain at least about 50 vol. % or at least about 75 vol. % hydrogen. Optionally, the hydrogen treat gas can be substantially free (less than about 1 vol. %) of impurities such as $H_2S$ and $NH_3$ and/or such impurities can be substantially removed from a treat gas prior to use. Hydrogen can be supplied co-currently with the input feed to reactor 102 or separately via a separate gas conduit.

In some embodiment, the total moles of hydrogen supplied to reactor 102 shall not exceed 10 times of the total moles of acetylene in acetylene-rich gas stream 101. In some embodiment, the total moles of hydrogen supplied to reactor 102 shall not exceed 5 times, or 2 times of the total moles of acetylene entered in acetylene-rich gas stream 101.

In some embodiments, reactor 102 may be cylindrical in shape. In some embodiments, reactor 102 may comprise a bottom end and a top end. In a non-limiting illustrative embodiment, the bottom end and the top end may be hemispherical or conical in shape. Suitable reactors for reactor 102 of system 100 include, for example, any convenient type of hydrogenation reactor, such as a fixed bed or a trickle-bed reactor and combinations thereof. In some embodiments, reactor 102 is an upright cylindrical separative reactor.

In some embodiments, reactor 102 is a trickle-bed reactor. In some embodiments, reactor 102 such as a trickle-bed reactor is an upflow reactor in which acetylene-rich gas stream 101 and hydrogen stream 103 are introduced into reactor 102 at or near the bottom end of reactor 102 flowing upwards and cooled recycled liquid solvent stream 116 at a top end of reactor 102 flowing downwards as shown in FIG. 1A to produce an acetylene-lean gas effluent 106 exiting reactor 102 at a top end. In some embodiments, reactor 102 such as a trickle-bed reactor is a downflow reactor in which acetylene-rich gas stream 101 and hydrogen stream 103 are introduced into reactor 102 at or near the top end of reactor 102 with as well as cooled recycled liquid solvent stream 116 at the top end of reactor 102 each flowing downwards as shown in FIG. 1B to produce acetylene-lean gas effluent 106 exiting reactor 102 at the bottom end. Although it is shown that acetylene-rich gas stream 101 and hydrogen stream 103 are individually fed into reactor 102, it is contemplated that any arrangement for introducing acetylene-rich gas stream 101 and hydrogen stream 103 into reactor 102 can be utilized in the present disclosure.

In some embodiments, reactor 102 includes a catalyst bed 104 (also referred to as "reaction zone") containing a hydrogenation catalyst and configured for receiving acetylene-rich gas stream 101 and hydrogen stream 103 flowing upwards and cooled recycled liquid solvent stream 116 flowing downwards. Although only one catalyst bed is shown for catalyst bed 104, any number of catalyst beds are contemplated for use in reactor 102. In some embodiments, cooled recycled liquid solvent stream 116 has a high selectivity to acetylene and low solubility for ethylene and the hydrogenation catalyst is suitable for an acetylene selective hydrogenation reaction.

Suitable solvents include liquid solvents such as, for example, aprotic polar solvents. In some embodiments, suitable aprotic polar solvents include, for example, N-alkylated lactam solvents, amide solvents, ketone solvents and the like and combinations thereof. Suitable N-alkylated lactam solvents include, for example, N-methyl-2-pyrrolidone, 1-ethyl-2-pyrrolidone, 1-propyl-2-pyrrolidone (branched or straight chained), or 1-butyl-2-pyrrolidone (branched or straight chained), and the like and mixtures thereof. Suitable amide solvents include, for example, dimethylacetamide, dimethylformamide, and the like and mixtures thereof. Suitable ketone solvents include, for example, acetone, and the like, or combinations thereof.

Suitable hydrogenation catalysts may be an acetylene hydrogenation catalyst that is a catalyst selective for hydrogenating acetylene. The hydrogenation catalyst may be any known catalyst for selectively hydrogenating acetylene. Commercial catalysts for acetylene hydrogenation are widely available, and the present disclosure is not limited to any specific composition recited herein. In some embodiments, a hydrogenation catalyst can include a hydrogenation metal in an amount between about 0.01 wt. % to about 5.0 wt. % on a support, wherein the hydrogenation metal is selected from a transition metal. In some embodiments, the metal can be platinum (Pt), palladium (Pd), rhodium (Rh), iridium (Ir), ruthenium (Ru), nickel (Ni), or a mixture thereof. In some embodiments, a transition metal is modified by one or more metals, selected from Group IB through IVA, such as zinc (Zn), indium (In), tin (Sn), lead (Pb), copper (Cu), silver (Ag), gold (Au), molybdenum (Mo), tungsten (W), titanium (Ti), niobium (Nb), ytterbium (Y), cobalt (Co) in an amount between about 0.01 wt. % and about 5 wt. %. Suitable supports include, for example, carbon materials such as activated carbon, carbon nanotubes, carbon fibers, etc.; aluminum oxides (aluminas); $SiO_2$, pure or doped with other metal oxides, synthetic or natural such as quartz; titanium silicate; $CaCO_3$; $BaSO_4$; and MgO. In some embodiments, supports include alpha-aluminas of various shapes and size (i.e. spheres, extrudates), with high degree of conversion to the alpha phase.

Suitable hydrogenation reaction conditions in reactor 102 include, for example, a temperature that may range between about 20° C. and about 250° C., or between about 40° C. and about 200° C., or between about 40° C. and about 120° C. In addition, reactor 102 can be operated at a high pressure which may range between approximately about 0.14 MPa (20 psig) and about 3.4 MPa (500 psig), or between about 1.0 MPa (150 psig) and about 2.8 MPa (400 psig). The liquid hour space velocity (LHSV) at the reactor inlet of reactor 102 can range between about 1 and about 100 $h^{-1}$, or between about 5 and about 50 $h^{-1}$, or about 5 and about 25 $h^{-1}$.

In operation, acetylene-rich gas stream 101 and hydrogen stream 103 enter reactor 102 and flow upwards to catalyst bed 104 and cooled recycled liquid solvent stream 116 flows downward to catalyst bed 104. In some embodiments, fresh catalyst may be added to catalyst bed 104 as needed (not shown). After allowing for sufficient mixing of cooled recycled liquid solvent stream 116, acetylene-rich gas stream 101 and hydrogen stream 103, acetylene from acetylene-rich gas stream 101 and hydrogen from hydrogen stream 103 are extracted into the liquid solvent, which further react in catalyst bed 104 in the presence of a hydrogenation catalyst and under the hydrogenation reaction conditions to selectively produce acetylene-lean gas effluent 106 and a heated liquid solvent effluent 108. Due to the hydrogenation reaction being an exothermic reaction, heat is transferred from the reaction to cooled recycled liquid solvent stream 116 to produce heated liquid solvent effluent 108.

In some embodiments, heated liquid solvent effluent 108 can comprise a liquid solvent and one or more impurities. For example, during the absorption and hydrogenation process discussed above, impurities such as heavy hydrocarbons including, for example, $C_4$ and $C_{5+}$ acetylenic and diolefinic species as well as coke and green oil can be formed.

Acetylene-lean gas effluent 106 is a vapor stream that is lean in acetylene and comprises ethylene and hydrogen gas. In some embodiments, acetylene-lean gas effluent 106 can be composed of greater than about 1 wt. % ethylene, or greater than about 5 wt. % ethylene or greater than about 20 wt. % ethylene and up to about 99 wt. % ethylene, and hydrogen gas. In some embodiments, acetylene-lean gas effluent 106 can be composed of about 0.01 wt. % to about 1 wt. % acetylene.

Acetylene-lean gas effluent 106 exits through a top portion of reactor 102 as an overhead stream that is rich in ethylene and having a reduced content of acetylene relative to acetylene-rich gas stream 101. Acetylene-lean gas effluent 106 may be passed to other processing and separation zones, the particulars of which are not necessary for an understanding and practicing of the present invention. For example, acetylene-lean gas effluent 106 may be sent to a separation unit external or internal to system 100 for extracting ethylene to send for further processing. Additionally, since acetylene-lean gas effluent 106 may include hydrogen, a portion of acetylene-lean gas effluent 106 may be recycled back to reactor 102 to provide hydrogen for other hydrogenation reactions. In some embodiments, heated acetylene-lean gas effluent 106 may be passed to one or more other reactors for further processing.

System 100 further includes a pump 110 and a heat exchanger 114. Heated liquid solvent effluent 108 exits reactor 102 at a bottom injection point and at an elevated temperature, e.g., a temperature ranging from about 100° C. to about 250° C., and is sent to pump 110. Pump 110 can be any suitable pump for increasing the pressure of heated liquid solvent effluent 108 for producing a pressurized heated liquid solvent stream 112. For example, pump 110 may be a rotary pump including an impeller, or alternatively may be any other suitable fluid pump including a centrifugal pump, a positive displacement pump, etc. Although only one pump is shown, any number of pumps can be included in system 100.

In some embodiments, heated liquid solvent effluent 108 can be combined with a cooled clean recycled solvent stream 132 as discussed below.

Pressurized heated liquid solvent stream 112 is split into two streams, namely, a first pressurized heated liquid solvent stream 112-1 and a second pressurized heated liquid solvent stream 112-2.

First pressurized heated liquid solvent stream 112-1 and cooled clean recycled solvent stream 132, when used, is passed to heat exchanger 114 to remove heat from first pressurized heated liquid solvent stream 112-1 and produce cooled recycled liquid solvent stream 116 having a temperature less than a temperature of first pressurized heated liquid solvent stream 112-1 and cooled clean recycled solvent stream 132 when used. In some embodiments, heat exchanger 114 is configured to remove reaction heat generated during the portion of the acetylene from acetylene-rich gas stream 101 being converted to ethylene. In some embodiments, heat exchanger 114 may be a shell-and-tube, plate-fin, microchannel, spiral wound, or any other suitable heat exchanger. In some embodiments, heat exchanger 114 can be configured to receive a heat transfer fluid provided at a temperature below the temperature of the hydrogenation reaction in order to cool first pressurized heated liquid solvent stream 112-1 being produced during the absorption and hydrogenation process. For example, heat exchanger 114 can be a shell and tube exchanger with first pressurized heated liquid solvent stream 112-1 flowing through the tubes with a heat transfer fluid such as water flowing through the shell side. Although only one heat exchanger is shown, any number of heat exchangers can be included in system 100.

Following the heat removal from first pressurized heated liquid solvent stream 112-1 in heat exchanger 114, cooled recycled liquid solvent stream 116 is sent to reactor 102 and re-used in another absorption and hydrogenation process with incoming acetylene-rich gas stream 101 and hydrogen stream 103 as discussed above.

In a non-limiting illustrative embodiment, system 100 can further include a solvent cleaning loop to remove any impurities that may be present in the heated liquid solvent effluent exiting reactor 102 following the absorption and hydrogenation process. As discussed above, during the absorption and hydrogenation process discussed above, impurities such as heavy hydrocarbons including, for example, $C_4$ and $C_{5+}$ acetylenic and diolefinic species as well as coke and green oil can be formed. Accordingly, to remove at least a portion of these impurities from the heated liquid solvent effluent 108 exiting reactor 102, second pressurized heated liquid solvent stream 112-2 can be sent to a separation unit 122 as discussed below.

In some embodiments, second pressurized heated liquid solvent stream 112-2 can be sent directly to separation unit 122. In some embodiments, second pressurized heated liquid solvent stream 112-2 can first be sent to a heat exchanger 118 before sending to separation unit 122 to remove heat from second pressurized heated liquid solvent stream 112-2 and produce a cooled liquid solvent stream 120 having a temperature less than a temperature of second pressurized heated liquid solvent stream 112-2. In some embodiments, heat exchanger 118 may be a shell-and-tube, plate-fin, microchannel, spiral wound, or any other suitable heat exchanger. In some embodiments, heat exchanger 118 can be configured to adjust the flow of second pressurized heated liquid solvent stream 112-2 to separation unit 122 at desired temperature for removing the impurities. For example, heat exchanger 118 can be a shell and tube exchanger with second pressurized heated liquid solvent stream 112-2 flowing through the tubes with a heat transfer fluid such as water flowing through the shell side. Although only one heat exchanger is shown, any number of heat exchangers can be included in system 100.

Cooled liquid solvent stream 120 is then split into two streams, namely, first cooled liquid solvent stream 120-1 and second cooled liquid solvent stream 120-2. Second cooled liquid solvent stream 120-2 is removed from system 100 as spent solvent.

First cooled liquid solvent stream 120-1 is sent to separation unit 122 to remove any impurities as discussed above. In some embodiments, separation unit 122 can be one of a distillation column or an absorption unit. In some embodiments, the distillation column can be operated in such a way that the impurities accumulate at the top of the column. This can be drawn off, and sent to be discarded. A clean liquid solvent stream 126 can exit the distillation column, i.e., separation unit 122, as a bottom end which contains relatively little to no impurities. In some embodiments, the absorption unit can be an absorption column that may absorb and remove the impurities from first cooled liquid solvent stream 120-1 to produce clean liquid solvent stream 126. The absorption unit may include active carbon, diatomite, zeolite, silica gel, and/or alumina.

In some embodiments, a fresh liquid solvent stream 124 can be injected into system 100 and combined with clean liquid solvent stream 126 to produce a clean recycled solvent stream 128. In some embodiments, fresh liquid solvent stream 124 can be any of the solvents discussed above. In some embodiments, fresh liquid solvent stream 124 can be dispensed from one or more storage tanks (not shown).

In some embodiments, clean recycled solvent stream 128 can be sent to a heat exchanger 130 to remove any heat present in clean recycled solvent stream 128 and produce cooled clean recycled solvent stream 132. In some embodiments, heat exchanger 130 may be a shell-and-tube, plate-fin, microchannel, spiral wound, or any other suitable heat exchanger. In some embodiments, heat exchanger 130 can be configured to receive a heat transfer fluid provided at a temperature below the temperature of clean recycled solvent stream 128 in order to cool clean recycled solvent stream 128. For example, heat exchanger 118 can be a shell and tube exchanger with second pressurized heated liquid solvent stream 112-2 flowing through the tubes with a heat transfer fluid such as water flowing through the shell side. Although only one heat exchanger is shown, any number of heat exchangers can be included in system 100. Cooled clean recycled solvent stream 132 can then be combined with heated liquid solvent effluent 108 and processed through the continuous solvent recycle loop as discussed above.

According to an aspect of the disclosure, a system comprises:

> an acetylene absorption and hydrogenation reactor configured to receive an acetylene-rich gas stream and a hydrogen stream flowing upwards or downwards to a reaction zone and a cooled recycled liquid solvent stream flowing downwards to the reaction zone, wherein the cooled recycled liquid solvent stream extracts acetylene in the acetylene-rich gas stream and hydrogen in the hydrogen stream and at least a portion of the acetylene is converted to ethylene in the presence of a hydrogenation catalyst and the hydrogen under hydrogenation reaction conditions to produce an acetylene-lean gas effluent and a heated liquid solvent effluent, and
>
> a first heat exchanger in fluid communication with the acetylene absorption and hydrogenation reactor for receiving the heated liquid solvent effluent, the first heat exchanger being configured to remove heat from the heated liquid solvent effluent and produce the cooled recycled liquid solvent stream as part of a continuous solvent recycle loop.

In one or more additional non-limiting illustrative embodiments, as may be combined with one or more of the preceding paragraphs, the system further comprises a pump in fluid communication with the acetylene absorption and hydrogenation reactor and the first heat exchanger, the pump being configured to increase the pressure of the heated liquid solvent effluent and produce a pressurized heated liquid solvent stream.

In one or more additional non-limiting illustrative embodiments, as may be combined with one or more of the preceding paragraphs, the system further comprises a second heat exchanger in fluid communication with the pump and configured to receive a first portion of the pressurized heated liquid solvent stream and remove heat from the first portion of the pressurized heated liquid solvent stream and produce a cooled recycled liquid solvent stream.

In one or more additional non-limiting illustrative embodiments, as may be combined with one or more of the preceding paragraphs, the system further comprises a separation unit in fluid communication with the second heat exchanger and configured to remove any impurities present in the cooled recycled liquid solvent stream and produce a clean liquid solvent stream.

In one or more additional non-limiting illustrative embodiments, as may be combined with one or more of the preceding paragraphs, the separation unit comprises one of a distillation column or an absorption unit.

In one or more additional non-limiting illustrative embodiments, as may be combined with one or more of the preceding paragraphs, the system further comprises a third heat exchanger in fluid communication with the separation unit.

In one or more additional non-limiting illustrative embodiments, as may be combined with one or more of the preceding paragraphs, the acetylene absorption and hydrogenation reactor is one of a fixed bed reactor or a trickle-bed reactor.

According to another aspect of the disclosure, a system comprises:

> an acetylene absorption and hydrogenation reactor configured to receive an acetylene-rich gas stream and a hydrogen stream flowing upwards or downwards to a reaction zone and a cooled recycled liquid solvent stream flowing downwards to the reaction zone, wherein the cooled recycled liquid solvent stream extracts acetylene in the acetylene-rich gas stream and hydrogen in the hydrogen stream and at least a portion of the acetylene is converted to ethylene in the presence of a hydrogenation catalyst and the hydrogen under hydrogenation reaction conditions to produce an acetylene-lean gas effluent and a heated liquid solvent effluent comprising a liquid solvent and one or more impurities,
>
> a first heat exchanger in fluid communication with the acetylene absorption and hydrogenation reactor for receiving at least a first stream of the heated liquid solvent effluent, the first heat exchanger being configured to remove heat from the first stream of the heated liquid solvent effluent and produce the cooled recycled liquid solvent stream, and
>
> a separation unit, in fluid communication with the first heat exchanger, configured to receive a second stream of the heated liquid solvent effluent and remove the one or more impurities from the liquid solvent and produce a clean liquid solvent stream.

In one or more additional non-limiting illustrative embodiments, as may be combined with one or more of the preceding paragraphs, the separation unit comprises one of a distillation column or an absorption unit.

In one or more additional non-limiting illustrative embodiments, as may be combined with one or more of the preceding paragraphs, the system further comprises a second heat exchanger in fluid communication with the separation unit and configured to remove any heat in the clean liquid solvent stream to produce a cooled clean recycled liquid solvent stream.

In one or more additional non-limiting illustrative embodiments, as may be combined with one or more of the preceding paragraphs, the system further comprises a pump in fluid communication with the acetylene absorption and hydrogenation reactor and the second heat exchanger, the pump being configured to increase the pressure of the cooled clean recycled liquid solvent stream and another heated liquid solvent effluent received from the acetylene absorption and hydrogenation reactor and produce a pressurized heated liquid solvent stream.

In one or more additional non-limiting illustrative embodiments, as may be combined with one or more of the preceding paragraphs, the acetylene absorption and hydrogenation reactor is one of a fixed bed reactor or a trickle-bed reactor.

According to yet another aspect of the disclosure, a continuous process comprises:

passing an acetylene-rich gas stream and a hydrogen stream to an acetylene absorption and hydrogenation reactor flowing upwards or downwards to a reaction zone in the acetylene absorption and hydrogenation reactor, passing a cooled recycled liquid solvent stream to the absorption and hydrogenation reactor flowing downwards to the reaction zone in the acetylene absorption and hydrogenation reactor, processing the acetylene-rich gas stream and the hydrogen stream with the cooled recycled liquid solvent stream to extract acetylene in the acetylene-rich gas stream and hydrogen in the hydrogen stream and convert at least a portion of the acetylene to ethylene in the presence of a hydrogenation catalyst and the hydrogen under hydrogenation reaction conditions to produce an acetylene-lean gas effluent and a heated liquid solvent effluent, and passing the heated liquid solvent effluent to a first heat exchanger to remove heat from the heated liquid solvent effluent to produce the cooled recycled liquid solvent stream as part of a continuous solvent recycle loop.

In one or more additional non-limiting illustrative embodiments, as may be combined with one or more of the preceding paragraphs, the continuous process further comprises passing the heated liquid solvent effluent to a pump to produce a pressurized heated liquid solvent stream.

In one or more additional non-limiting illustrative embodiments, as may be combined with one or more of the preceding paragraphs, the continuous process further comprises:

splitting the pressurized heated liquid solvent stream into a first pressurized heated liquid solvent stream and a second pressurized heated liquid solvent stream, passing the first pressurized heated liquid solvent stream to the first heat exchanger, and passing the second pressurized heated liquid solvent stream to a second heat exchanger to adjust the temperature of the second pressurized heated liquid solvent stream to a given temperature for removing any impurities present in the second pressurized heated liquid solvent stream.

In one or more additional non-limiting illustrative embodiments, as may be combined with one or more of the preceding paragraphs, the continuous process further comprises passing the second pressurized heated liquid solvent stream from the second heat exchanger to a separation unit to remove any impurities present in the second pressurized heated liquid solvent stream and produce a clean liquid solvent stream.

In one or more additional non-limiting illustrative embodiments, as may be combined with one or more of the preceding paragraphs, the separation unit comprises one of a distillation column or an absorption unit.

In one or more additional non-limiting illustrative embodiments, as may be combined with one or more of the preceding paragraphs, the continuous process further comprises adding a fresh liquid solvent stream to the clean liquid solvent stream to produce a clean recycled solvent stream.

In one or more additional non-limiting illustrative embodiments, as may be combined with one or more of the preceding paragraphs, the continuous process further comprises:

passing the clean recycled solvent stream to a third heat exchanger to remove any heat in the clean recycled solvent stream and produce a cooled clean recycled solvent stream, and combining the cooled clean recycled solvent stream with the heated liquid solvent effluent.

In one or more additional non-limiting illustrative embodiments, as may be combined with one or more of the preceding paragraphs, the hydrogenation reaction conditions comprise a temperature of about 50° C. and about 250° C., a pressure of about 0.69 MPa and about 3.4 MPa and a liquid hour space velocity (LHSV) at the reactor inlet of the acetylene absorption and hydrogenation reactor of about 1 and about 100 $h^{-1}$.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present disclosure and are disclosed herein just as if each and every such sub-combination was individually and explicitly disclosed herein.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A continuous process, comprising:

passing an acetylene-rich gas stream and a hydrogen stream to a reactor flowing upwards or downwards to a reaction zone in the reactor;

passing a cooled recycled liquid solvent stream to the reactor flowing downwards to the reaction zone in the reactor, processing the acetylene-rich gas stream and the hydrogen stream with the cooled recycled liquid solvent stream to extract acetylene in the acetylene-rich gas stream and hydrogen in the hydrogen stream and convert at least a portion of the acetylene to ethylene in the presence of a hydrogenation catalyst and the hydrogen under hydrogenation reaction conditions to produce an acetylene-lean gas effluent and a heated liquid solvent effluent; and passing the heated liquid solvent effluent to a first heat exchanger to remove heat from the heated liquid solvent effluent to produce the cooled recycled liquid solvent stream as part of a continuous solvent recycle loop.

2. The continuous process according to claim 1, further comprising passing the heated liquid solvent effluent to a pump to produce a pressurized heated liquid solvent stream.

3. The continuous process according to claim 1, further comprising:

splitting the pressurized heated liquid solvent stream into a first pressurized heated liquid solvent stream and a second pressurized heated liquid solvent stream;

passing the first pressurized heated liquid solvent stream to the first heat exchanger; and passing the second pressurized heated liquid solvent stream to a second heat exchanger to adjust the temperature of the second pressurized heated liquid solvent stream to a given temperature for removing any impurities present in the second pressurized heated liquid solvent stream.

4. The continuous process according to claim 3, further comprising passing the second pressurized heated liquid solvent stream from the second heat exchanger to a separation unit to remove any impurities present in the second pressurized heated liquid solvent stream and produce a clean liquid solvent stream.

5. The continuous process according to claim 4, wherein the separation unit comprises one of a distillation column or an absorption unit.

6. The continuous process according to claim 4, further comprising adding a fresh liquid solvent stream to the clean liquid solvent stream to produce a clean recycled solvent stream.

7. The continuous process according to claim 6, further comprising:

passing the clean recycled solvent stream to a third heat exchanger to remove any heat in the clean recycled solvent stream and produce a cooled clean recycled solvent stream; and combining the cooled clean recycled solvent stream with the heated liquid solvent effluent.

8. The continuous process according to claim 1, wherein the hydrogenation reaction conditions comprise a temperature of about 50° C. and about 250° C., a pressure of about 0.69 MPa and about 3.4 MPa and a liquid hour space velocity (LHSV) at the reactor inlet of the acetylene absorption and hydrogenation reactor of about 1 and about $100\,h^{-1}$.

9. The continuous process according to claim 1, wherein the reactor is one of a fixed bed reactor and a trickle-bed reactor.

* * * * *